United States Patent [19]

Ardaillon et al.

[11] Patent Number: 5,225,238
[45] Date of Patent: Jul. 6, 1993

[54] METHOD FOR COATING ACTIVE PRINCIPLES WITH A PH-SENSITIVE POLYMER

[75] Inventors: Pierre Ardaillon, Saint-Priest; Christian Prud'Homme, Lyons, both of France

[73] Assignee: Rhone-Poulenc Nutrition Animale, Commentry, France

[21] Appl. No.: 666,313

[22] Filed: Mar. 8, 1991

[30] Foreign Application Priority Data

Mar. 8, 1990 [FR] France ................................ 90 02973

[51] Int. Cl.⁵ ................................................ A61K 9/26
[52] U.S. Cl. ........................................ 427/3; 427/212; 427/421; 426/656
[58] Field of Search ............................ 427/3, 212, 421; 426/656

[56] References Cited

U.S. PATENT DOCUMENTS

| | | | |
|---|---|---|---|
| 3,935,326 | 1/1976 | Groppenbacher et al. | 427/3 |
| 3,960,757 | 6/1976 | Morishita et al. | 427/3 |
| 4,017,647 | 4/1977 | Ohno et al. | 427/3 |
| 4,105,615 | 8/1978 | Balatan | 426/131 |
| 4,497,847 | 2/1985 | Kurihara et al. | 427/3 |
| 4,687,676 | 8/1987 | Wu et al. | 427/3 |
| 4,832,967 | 5/1989 | Autant et al. | 426/310 |
| 4,876,097 | 10/1989 | Autant et al. | 426/74 |
| 4,877,621 | 10/1989 | Ardaillon et al. | 424/498 |
| 4,937,083 | 6/1990 | Itagaki et al. | 426/74 |
| 4,976,976 | 12/1990 | Itagaki et al. | 426/72 |
| 5,023,108 | 6/1991 | Bagaria et al. | 427/3 |
| 5,025,004 | 6/1991 | Wu et al. | 427/3 |

FOREIGN PATENT DOCUMENTS

| | | |
|---|---|---|
| 0188953 | 7/1986 | European Pat. Off. |
| 0260186 | 3/1988 | European Pat. Off. |
| 0336713 | 10/1989 | European Pat. Off. |
| 80/00659 | 4/1980 | PCT Int'l Appl. |

*Primary Examiner*—Shrive Beck
*Assistant Examiner*—Diana L. Dudash
*Attorney, Agent, or Firm*—Finnegan, Henderson, Farabow, Garrett & Dunner

[57] ABSTRACT

A new method of coating an active principle which comprises the step of coating an active principle with an aqueous emulsion or dispersion containing one or more pH-sensitive polymers.

20 Claims, No Drawings

METHOD FOR COATING ACTIVE PRINCIPLES WITH A PH-SENSITIVE POLYMER

The present invention relates to a method for coating active principles with a formulation containing one or more pH-sensitive polymers. It relates more particularly to a method for coating, preferably by spraying, medicament and/or foodstuff active principles with an aqueous emulsion or suspension of one or more pH-sensitive polymers.

It is well-known to coat active principles with pH-sensitive polymers, and pH-sensitive polymers mixed with a hydrophobic substance, for example, stearic acid, and/or a water-insoluble polymer, for example, ethylcellulose. These coatings are described as applied to animal feeds in U.S. Pat. No. 4,832,967, EP 260,186 and EP 188,953, the disclosure of the U.S. Pat. which is specifically incorporated by reference herein.

According to these documents, spherical particles of methionine and/or lysine are coated by the fluidized-bed technique using a solution of pH-sensitive polymer dissolved in one or more organic solvents, for example, halogenated solvents, alcohols or ethers. This technique permits easy spraying of the pH-sensitive polymer or polymers, but has the disadvantage of introducing significant amounts of solvents. The solvent introduction is approximately 20 to 100 g of solvent(s) per 1 g of pH-sensitive polymer. The introduction of solvents to products intended for animal feeds for which the ecotoxicity has not been determined is an important drawback of the prior art.

The present invention has made it possible to coat active principles, such as amino acids or vitamins, using pH-sensitive polymers, while minimizing the use of organic solvents incompatible with biological media.

In a preferred embodiment, the present invention relates to a method for coating medicament and/or foodstuff active principles with one or more pH-sensitive polymers by spraying an aqueous emulsion or dispersion of the pH-sensitive polymer or polymers onto said active principles. This coating can be effected despite the significant solubility in water of some active principles, such as lysine or its derivatives. The medicament and/or foodstuff active principles to be coated are preferably in the form of granules having a diameter of between about 0.3 and 3 mm.

The deposition of the coating agent from the aqueous emulsion can permit a significant cost savings in the implementation of the method because it can minimize or remove the need for recovery installations to remove unwanted solvents. Recovery installations of this type can be costly from the standpoint of security and investment. The method of the present invention can also enable the productivities to be improved over the productivities of the prior art methods.

The pH-sensitive polymers used in the method according to the present invention are preferably selected from:
- the polyvinyl acetals of acetylacetic esters substituted by nitrogen-containing dialkyl groups, such as the diethylamino group,
- the copolymers of dialkylaminoalkyl acrylates and methacrylates and an acrylic or methacrylic acid or ester, and
- the copolymers of styrene or acrylonitrile with vinylpyridine, or the isomers or the derivatives thereof.

Among all of the polymers listed above, it is preferable to use the copolymers of styrene with 2-vinylpyridine.

The medicament active principles are preferably selected from vitamins, antibiotics, antiparasitic compounds and hormones. The foodstuff active principles are preferably selected from the essential amino acids, for example, methionine and/or lysine and/ or tryptophan.

Fillers, which may be lamellar and which facilitate disintegration in the digestive tract, may be added to the active principles. The fillers may or may not be pH-sensitive. These fillers are preferably selected from: talc and/or silica and/or carbonates and/or complex polyphosphates, preferably those based on $Na_2O$, $CaO$, $P_2O_5$ and $Al_2O_3$.

Binders, selected from fatty acids or fatty esters, cellulose (for example, cellulose marketed under the name Avicel) or its derivatives, preferably ethylcellulose or carboxymethylcellulose, and also basic copolymers, may also be added to the active principles. The active principle or principles and the additives as a whole form the core of the granule. The granule is then coated by the pH-sensitive polymer or polymers, preferably sprayed in the form of an aqueous emulsion.

These medicament or foodstuff active principles which optionally contain an additive and are coated with pH-sensitive polymer are particularly useful for feeding ruminants because they can remain intact or be only slightly degraded during transit through the rumen. The active principles are liberated in the abomasum and/or the intestine of the ruminants.

Coating of the active principles can be effected by spraying an aqueous emulsion or dispersion containing the pH-sensitive polymer or polymers. This emulsion or dispersion can be produced by mixing an organic solution containing the pH-sensitive polymer or polymers and an aqueous solution containing an emulsifier.

The coating emulsion may also contain additives including those mentioned above, as well as antistatic agents, plasticizers, colorants or appetite stimulants. It is preferable to use an aqueous dispersion containing the pH-sensitive polymer or polymers and a hydrophobic substance. This aqueous dispersion may optionally contain a water-insoluble polymer.

The hydrophobic substance is preferably selected from fatty acids containing 12 to 22 carbon atoms, for example, stearic acid or behenic acid. The emulsifier may be selected from fatty acid esters or fatty acid salts. If the emulsifier is a fatty acid salt, the emulsifier may be produced "in situ" by converting the fatty acid to a salt by means, for example, of a base selected from alkali metal hydroxides and ammonium hydroxide.

The optional water-insoluble polymer is preferably selected from water-insoluble cellulose ethers and esters, more preferably ethylcellulose, cellulose acetate, cellulose propionate and cellulose acetobutyrate.

The organic solvent for the pH-sensitive polymer or polymers can be selected from straight-chain or branched alcohols containing at least four carbon atoms, esters such as alkyl acetates, ethers, such as isopropyl ether, ketones, such as methyl isobutyl ketone, and halogenated solvents, such as tetrachloroethane, trichloroethane, dichloroethane, chloroform and dichloromethane.

The emulsion can be prepared by mixing a predominant aqueous phase and an organic phase. It is preferable that the aqueous phase represents about 60 to 97% by volume and the organic phase represents about 3 to 40% by volume.

The emulsifier and/or one of its precursors permitting "in situ" formation of the emulsifier are contained within the aqueous phase. The aqueous phase contains preferably about 0 to 10% by weight of fatty acid esters or salts, and/or it contains about 0 to 1% by weight of an alkali metal hydroxide or ammonium hydroxide. For the emulsion to form at least one of the two groups of constituents, either the emulsifier or the alkali metal hydroxide or ammonium hydroxide and the fatty acid must be present. The minimum amount of emulsifier added or formed "in situ", calculated based upon sodium hydroxide, is generally about 0.2% by weight.

The organic phase can be obtained by dispersing or dissolving a solid mixture in the solvent for the pH-sensitive polymer. The solid mixture preferably has the following composition, by weight:
- about 10 to 70% of pH-sensitive polymer or polymers,
- about 30 to 90% of one or more hydrophobic substances, and
- about 0 to 20% of one or more water-insoluble polymers.

The percentage of the various phases are preferably within the following limits:
- aqueous phase, about 50 to 97% by weight,
- solid phase, about 2 to 30% by weight, and
- organic solvent, about 1 to 20% by weight.

The percentages of the various phases are more preferably within the following limits:
- aqueous phase, about 72 to 87% by weight,
- solid phase, about 10 to 20% by weight, and
- organic solvent, about 3 to 8% by weight.

The organic phase, obtained after dispersing or dissolving the solid phase in the organic solvent, is mixed with the previously prepared aqueous phase. If the organic phase does not contain fatty acid, the aqueous phase may contain an emulsifier; alternatively, if the organic phase contains a fatty acid, the aqueous phase may contain an alkali metal hydroxide or ammonium hydroxide and/or an emulsifier.

The emulsion is produced by introducing the organic phase into the aqueous phase or vice versa.

After obtaining the emulsion, it can be subjected to an evaporation or a distillation to remove virtually all of the organic solvent. This removal can be effected at a temperature of between about 70° and 100° C., at atmospheric pressure. It is possible to work at lower temperatures if the pressure is below atmospheric pressure. Those skilled in the art are capable of adapting the operating conditions, temperature, pressure and duration of operation, to obtain the most economical method.

At the end of the distillation, the emulsion which is preferably obtained, contains less than about 30% solids; less than about 0.5% organic solvent and preferably less than about 0.1% organic solvent. The emulsion obtained can then be sprayed onto a bed of granules to be coated using the fluidized-bed technique. The fluidized-bed technique may be of the WURSTER type, as described in U.S. Pat. No. 2,799,241 and EP 188,953, the disclosure of the U.S. Pat. is specifically incorporated by reference herein.

The coated granules obtained after spraying can be used for feeding ruminants or treating ruminants with medicaments.

The active principle that is liberated in the rumen over a 24 hour period is preferably less than or equal to 10 percent, more preferably less than or equal to 5 percent.

Preparation of the coated granules will be described more fully with the aid of the following examples. These examples are not to be regarded as limiting the invention in any manner.

EXAMPLE 1

The following were mixed in a heated vessel fitted with a magnetic stirring system:
- 80 g of butyl acetate, and
- 88 g of stearic acid (PRIFRAC 2981 ® marketed by UNICHEMA).

After observing the complete dissolution of the stearic acid,
- 22 g of a copolymer of 2-vinylpyridine (57% by weight) and styrene (43% by weight) were added to the mixture.

This polymer was characterized by its inherent viscosity: 1.36 dl/g (measured at 25° C, in solution in dimethylformamide, at a concentration of about 0.5 g of copolymer per 100 ml).

After heating for a few minutes at about 90°–100° C., a homogeneous solution was obtained.

495 g of demineralized water were charged into another vessel having a capacity of 2 liters and 4.2 mls of a 10% aqueous sodium hydroxide solution were then added.

The contents of the vessel were then heated to about 85° C. and mixed using an apparatus of the POLYTRON type rotating at 11,000 revolutions per minute. The organic solution described above, having been charged into a dropping funnel kept at about 95° C., was then added to the aqueous solution over a period of seven minutes.

After all of the organic solution was run into the aqueous solution, the emulsion obtained was diluted with 495 g of demineralized water and mixed using the Polytron mixer for an additional four minutes.

Virtually all of the butyl acetate present in the emulsion was then removed. The removal of the butyl acetate was carried out in the following manner: magnetic stirring of this mixture was continued and the mixture was brought to a boil until a loss in weight, due to evaporation, equal to 34% by weight of the initial emulsion was recorded. After removal of the butyl acetate the solids content, by weight, of the mixture was brought to about 10% by dilution with demineralized water.

Using vapor phase chromatographic analysis, it was established that the residual concentration by weight of butyl acetate in the emulsion was below about 0.15%. The emulsion was kept at about 70°–75° C. for 18 hours, with magnetic stirring, before being used.

500 g of spherical granules having an average diameter of about 2 mm and assaying about 57% of lysine hydrochloride and about 16% of methionine are charged into a UNIGLATT ® spray-coating apparatus fitted with a WURSTER system.

The emulsion, which was kept at about 87° C. and stirred gently, was sprayed under the following spraying conditions into the fluidized bed formed by the granules:
- flow rate of the air used for fluidization: about 130 m$^3$/h,
- temperature of the air used for fluidization (outlet): about 37° C.,

- pressure of the air used for spraying: about 1.5 bars,
- temperature of the air used for spraying: about 83° C.,
- flow rate of the emulsion: about 12 ml/min, and
- spraying time: about 51 min.

The degree of protection provided by the coating skin thus deposited was evaluated using an in-vitro test comprising stirring a predetermined amount of coated granules in an aqueous solution buffered to a pH of about 6 and kept at about 40° C. The amount of lysine hydrochloride liberated into the medium after 6 hours and 24 hours was determined. The results are indicated in Table I.

EXAMPLE 2

Example 1 was repeated, with the following modifications:
- The butyl acetate was removed by evaporation until a loss in weight of the emulsion equal to about 47% of the initial weight was established.
- After the evaporation of the butyl acetate, the emulsion was not re-diluted, in order to retain a solids content of about 20% by weight for the coating.
- The concentration by weight of residual butyl acetate, after evaporation, was below about 0.2% (by vapor phase chromatography analysis).
- The emulsion was used immediately after its preparation to produce a coating of amino acids under conditions identical to those which are described above in Example 1.
- The spraying time was no more than about 34 minutes, for an emulsion flow rate of about 9.3 ml/min.

Granules having a good resistance to the aqueous medium at a pH of about 6 and at about 40° C. were obtained (Table I).

EXAMPLE 3

Example 1 was repeated, exactly, omitting the evaporation and storage stages. The emulsion obtained was used immediately after its preparation to coat the amino acid granules described above.

EXAMPLE 4

In order to demonstrate that the removal of the organic solvent leads to more stable emulsions, Example 3 was repeated exactly and the emulsion was stored for about 19 hours at about 72° C. before it was used to produce a coating under the same conditions as in Example 1.

The quality of the product (see Table I) indicates that the emulsion was less stable than that in Example 1.

EXAMPLE 5

The following were mixed in a heated vessel fitted with a magnetic stirring system:
- 80 g of butyl acetate, and
- 88 g of stearic acid (PRIFAC® 2981).

After complete dissolution of the stearic acid,
- 22 g of a copolymer of 2-vinylpyridine (70% by weight) and styrene (30% by weight) were added to the mixture.

This copolymer was characterized by its inherent viscosity: $[\mu]_{inh}$ 1.20 dl/g (at about 25° C., in solution in dimethylformamide, at a concentration of about 0.5 g per 100 ml).

After heating for a few minutes at about 90°-100° C., a homogeneous solution was obtained.

495 g of demineralized water, to which 4.2 mls of a 10% aqueous sodium hydroxide solution have been added, were charged into another vessel having a capacity of 2 liters.

The contents of this vessel were then heated to about 85° C. and mixed using the turbine stirrer of a POLYTRON type apparatus rotating at 11,000 revolutions per minute.

The above organic solution, previously charged into a dropping funnel kept at about 95° C., was then added over a period of about seven minutes.

After the solution was run in, the emulsion obtained was diluted with 104 g of demineralized water and mixed for approximately four more minutes using the POLYTRON turbine stirrer.

Virtually all of the butyl acetate present in the emulsion was then removed in the following way:

The vessel in which the emulsion was kept under magnetic stirring was fitted with a distillation column, a descending condenser and a receiver.

After distillation at atmospheric pressure, a mixture formed of two immiscible and clear liquid phases representing in total about 18% by weight of the initial emulsion was collected in the receiver.

The solids content of the emulsion thus obtained was about 21% by weight.

Its residual butyl acetate concentration, determined by vapor phase chromatography, was about 0.05%.

The emulsion was kept for about 19 hours at about 70°-75° C., under gentle magnetic stirring, before being sprayed in a UNIGLATT® spray-coating apparatus fitted with a WURSTER system and charged with 500 g of amino acid granules identical to those of Example 1.

During spraying, stirring of the emulsion, which was then heated to about 87° C., was continued.

The spraying conditions were as follows:
- flow rate of the air used for fluidization: about 130 m³/h,
- temperature of the air used for fluidization (outlet): about 37° C.,
- pressure of the air used for spraying: about 1.5 bar,
- temperature of the air used for spraying: about 87° C.,
- emulsion flow rate: about 9 ml/minute, and
- spraying time: about 39 minutes.

The granules obtained were characterized in the same way as in the preceding examples.

These results are indicated in Table I.

TABLE I

| Sample | Emulsion % by weight of butyl acetate | Storage time (h) before use | Proportion of coating % | In vitro test: pH 6/40° C. % of lysine liberated after 6 h | 24 h | In vitro test: pH 2/40° C. % of lysine liberated after 15 min | 30 min |
|---|---|---|---|---|---|---|---|
| Example 1 | 0.13 | 18 | 10.4 | 1.9 | 3.7 | 87 | 100 |
| Example 2 | 0.2 | 0 | 8.7 | 1.4 | 2.7 | 90 | 100 |
| Example 3 | 3.9 | 0 | 9.5 | 0.5 | 1.5 | 83 | 100 |
| Example 4 | 2.5 | 19 | 10.4 | 75 | 92 | 92 | 100 |

TABLE I-continued

| Sample | Emulsion % by weight of butyl acetate | Emulsion Storage time (h) before use | Proportion of coating % | In vitro test: pH 6/40° C. % of lysine liberated after 6 h | In vitro test: pH 6/40° C. % of lysine liberated after 24 h | In vitro test: pH 2/40° C. % of lysine liberated after 15 min | In vitro test: pH 2/40° C. % of lysine liberated after 30 min |
|---|---|---|---|---|---|---|---|
| Example 5 | 0.05 | 19 | 11.6 | 0.5 | 2.3 | 90 | 100 |

What is claimed is:

1. A method for coating at least one active principle with one or more pH-sensitive polymers insoluble in water comprising the step of,
spray coating at least one active principle with an aqueous emulsion or dispersion containing one emulsifier, less than 0.5% by weight of organic solvent and a pH-sensitive polymer or polymers, obtained by mixing an organic solvent phase, containing 10% to 70% by weight of the pH-sensitive polymer or polymers and 30% to 90% by weight of one or more hydrophobic substances, and about 0 to 20% by weight of one or more water insoluble polymers and an aqueous solution, containing up to 10% by weight of an emulsifier or up to about 1% by weight of an alkali metal hydroxide or ammonium hydroxide permitting in situ formation of the emulsifier, wherein, the emulsifier represents at least 0.2% by weight of sodium hydroxide equivalent, followed by removal of the organic solvent,
wherein said coated active principle is suitable for treating or feeding a ruminant.

2. The method according to claim 1, wherein the active principle is selected from medicaments, foodstuffs and combinations thereof.

3. The method according to claim 1, wherein the emulsion to be sprayed contains less than about 0.1% by weight of organic solvent.

4. The method according to claim 1, wherein the organic solvent removal is by evaporation or distillation.

5. The method according to claim 1, wherein the emulsion or dispersion further contains a water insoluble polymer.

6. The method according to claim 1, wherein the active principle is an amino acid selected from methionine, lysine, one of its derivatives or any combination thereof.

7. The method according to claim 1, wherein the hydrophobic substance is selected from at least one fatty acid containing 12 to 22 carbon atoms.

8. The method according to claim 1, wherein the hydrophobic substance is stearic acid.

9. The method according to claim 5, wherein the water-insoluble polymer is selected from water-insoluble cellulose ethers and esters.

10. The method according to claim 1, wherein the emulsifier is selected from fatty acid salts and esters.

11. The method according to claim 1, wherein the emulsifier precursor permitting "in situ" formation of the emulsifier is selected from alkali metal hydroxides or ammonium hydroxide.

12. The method according to claim 1, wherein an active principle and a filler selected from talc, silica, carbonates, complex polyphosphates or combinations thereof are coated with said aqueous emulsion or dispersion.

13. The method according to claim 12, wherein the filler contains a complex polyphosphate based on $Na_2O$, $CaO$, $P_2O_5$ or $Al_2O_3$.

14. The method according to claim 1, wherein an emulsion comprises a mixture of pH-sensitive polymer, ethylcellulose, stearic acid, sodium stearate and water is sprayed onto granules of methionine and/or lysine.

15. The method according to claim 1, wherein the emulsion also contains one or more additives selected from fillers, antistatic agents, plasticizers, colorants and appetite stimulants.

16. The method according to claim 14, wherein the emulsion also contains one or more additives selected from fillers, antistatic agents, plasticizers, dyes and appetite stimulants.

17. The method according to claim 1, wherein the emulsion is prepared by mixing about 97 to 60% by volume of an aqueous phase and about 3 to 40% by volume of an organic phase.

18. The method according to claim 1, wherein said organic phase is formed from a solid mixture and an organic solvent and wherein the percentage, by weight, of the various constituents is within the following limits:
- aqueous solution phase about 50 to 97%,
- solid mixture about 2 to 30%, and
- organic solvent about 1 to 20%.

19. The method according to claim 18, wherein the percentage, by weight, of the various constituents is within the following limits:
- aqueous solution about 72 to 87%,
- solid mixture about 10 to 20%, and
- organic solvent about 3 to 8%.

20. The method according to claim 1, wherein the percent active principle liberated from the resultant coated active principle over a 24 hour period in the rumen is less than or equal to 5% by weight.

* * * * *

UNITED STATES PATENT AND TRADEMARK OFFICE
CERTIFICATE OF CORRECTION

PATENT NO. : 5,225,238
DATED : July 06, 1993
INVENTOR(S) : Pierre Ardaillon et al.

It is certified that error appears in the above-indentified patent and that said Letters Patent is hereby corrected as shown below:

On the title page, item (54) and column 1:

In the title, line 2, change "PH-SENSITIVE" to "pH-SENSITIVE".

Claim 1, column 7, line 15, delete ",".

Claim 1, column 7, line 29, delete "," (second occurrence).

Claim 11, column 8, line 13, delete quotation marks around "in situ".

Signed and Sealed this

Twenty-sixth Day of April, 1994

Attest:

BRUCE LEHMAN

*Attesting Officer*    *Commissioner of Patents and Trademarks*